(12) United States Patent
Langer et al.

(10) Patent No.: US 8,530,676 B2
(45) Date of Patent: Sep. 10, 2013

(54) PROCESS FOR PRODUCING VINYLENE CARBONATE

(75) Inventors: Reinhard Langer, Tönisvorst (DE); Anke Beckmann, Köln (DE); Paul Wagner, Düsseldorf (DE); Heinrich Grzinia, Erkelenz (DE); Marielouise Schneider, Leverkusen (DE); Ulrich Notheis, Dormagen (DE); Lars Rodefeld, Leverkusen (DE); Nikolaus Müller, Monheim (DE)

(73) Assignee: SALTIGO GmbH, Langenfeld (DE)

( * ) Notice: Subject to any disclaimer, the term of this patent is extended or adjusted under 35 U.S.C. 154(b) by 506 days.

(21) Appl. No.: 11/920,171

(22) PCT Filed: May 4, 2006

(86) PCT No.: PCT/EP2006/004157
§ 371 (c)(1), (2), (4) Date: Jan. 6, 2009

(87) PCT Pub. No.: WO2006/119911
PCT Pub. Date: Nov. 16, 2006

(65) Prior Publication Data
US 2009/0234141 A1     Sep. 17, 2009

(30) Foreign Application Priority Data

May 12, 2005   (DE) .................. 10 2005 021 968

(51) Int. Cl.
*C07D 317/08*     (2006.01)

(52) U.S. Cl.
USPC .................................... 549/229; 549/230

(58) Field of Classification Search
USPC .................................... 549/229, 230
See application file for complete search history.

(56) References Cited

U.S. PATENT DOCUMENTS 6,193,765 B1 *   2/2001   Nakanishi et al. ........... 29/623.1
6,395,908 B1 *   5/2002   Seifert et al. ................. 549/229

FOREIGN PATENT DOCUMENTS

JP    2000/0026449    1/2000

OTHER PUBLICATIONS

Newman et al., J. Am. Chem. Soc., 75, 1263-1264, 1953.*
Newman et al., J. Am. Chem. Soc., 77, 3789-3793, 1955.*

* cited by examiner

*Primary Examiner* — Andrew D Kosar
*Assistant Examiner* — Raymond Covington
(74) *Attorney, Agent, or Firm* — Michael A. Miller

(57) ABSTRACT

The present invention relates to the industrial production of vinylene carbonate (VC) by elimination of hydrogen chloride from chloroethylene glycol carbonate (CGC) with tertiary amines in the absence of relatively large amounts of additional solvent.

5 Claims, No Drawings

PROCESS FOR PRODUCING VINYLENE CARBONATE

The present invention relates to the industrial production of vinylene carbonate (VC) by elimination of hydrochloride from chloroethylene glycol carbonate (CGC) in the liquid phase.

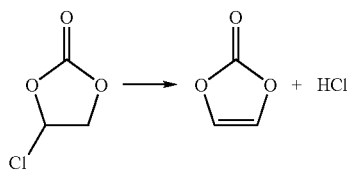 [SMILES: O=C1OCC(Cl)O1 ; O=c1occo1 ; Cl]

Vinylene carbonate is an important intermediate for the production of chemicals, pharmaceutical products, crop protection agents and in particular for polymers, coatings and battery electrolytes.

Vinylene carbonate is produced by the known method by eliminating hydrogen chloride from chloroethylene glycol carbonate by means of tertiary amines, in particular triethylamine.

Chloroethylene glycol carbonate is obtained by free radical chlorination of ethylene glycol carbonate by means of chlorine or sulphuryl chloride.

This synthesis was published for the first time in 1953 by Newman and Addor (JACS, 1953, page 1263; JACS 1955, page 3789).

Ethylene glycol carbonate (GC) was photochlorinated as such by means of ultraviolet light at 60-70° C., and the resulting CGC was purified by vacuum distillation.

Newman and Addor obtained VC by elimination by means of triethylamine in boiling ether (b.p. 35° C.) the mixture having been heated overnight.

The isolation was effected by filtering off the triethylammonium chloride and then carrying out distillation, which gave a crude VC in a yield of 59%, which crude VC had to be purified by further distillation.

JP 2000/026449 describes the elimination in high-boiling solvents (b.p. 170-300° C.); the reaction is explicitly effected with triethylamine in dibutyl carbonate for 20 hours at 50° C.

After the ammonium chloride has been filtered off and excess triethylamine distilled off, crude VC is isolated by simple distillation. In order to remove traces of amines, the VC is poured over a silica gel column. Finally, a purifying distillation is carried out. The chlorine content of the VC thus obtained is stated as 29 ppm, whereas comparative samples contain >3000 ppm. The yield is 56%.

DE-A 19955944 describes the elimination in GC as a solvent (b.p. 243-244° C.). CGC is initially introduced in GC and reacted in 1.5 hours by addition of triethylamine at 60° C. After excess triethylamine has been distilled off at 40° C. and evaporation has been effected via a thin-film evaporator at 100° C., a colourless mixture of VC and GC is obtained in a yield of 73%. No data are given concerning the purity.

The reactions of CGC in the liquid phase all suffer from the decomposability of the VC, which is explicitly mentioned in DE-A 199 55 944 A1. Accordingly, it decomposes in hours at above 60° C. and in minutes at above 80° C. The resulting polymers make it more difficult to separate off salts and the exothermic decomposition makes the scale-up of such processes problematic.

What is particularly difficult is that both the elimination reaction of CGC with triethylamine to give VC and ammonium chloride and the decomposition of the VC become substantially more rapid with increasing temperature.

A process which gives higher conversions and selectivities at low temperatures and permits easy isolation of the VC and of the ammonium salt, not least by good filterability of the salt and good stirrability of the reaction mixtures, would be desirable.

The invention therefore relates to the provision of a process for the production of vinylene carbonate, in which the VC can be produced in increased yield with better isolation of the VC from the reaction mixture.

Surprisingly, it was found that the desired process properties are achieved if the procedure is effected without a solvent or with very little solvent, i.e. vinylene carbonate itself serves as the solvent.

The invention relates to a process for the production of vinylene carbonate by elimination of hydrogen chloride from chloroethylene glycol carbonate (CGC) with tertiary amines, characterized in that the reaction is carried out at between 30 and 60° C. in vinylene carbonate as reaction medium, which optionally also contains up to 50% by weight of further solvent, based on the reaction medium.

The amount of inert solvent in the reaction mixture is below 10% by weight, preferably below 3% by weight, particularly preferably below 1% by weight, and very particularly preferably the procedure is effected in the absence of a solvent. The stated percentages by weight are based on the reaction medium.

Possible inert solvents are, for example, aliphatic and aromatic hydrocarbons from the group consisting of the $C_1$-$C_{10}$-alkanes or cycloalkanes and benzene which is optionally polysubstituted by $C_1$-$C_{10}$-alkyl or cycloalkyl radicals, such as, for example, toluene or xylene, halogenated hydrocarbons from the group consisting of the chlorobenzenes or $C_1$-$C_{10}$-chloroalkanes, such as, for example, chlorobenzene or methylene chloride. The solvents may contain ether, nitrile and ester functions.

Particularly preferred solvents are toluene from the group consisting of the aromatic hydrocarbons, methylene chloride from the group consisting of the halogenated hydrocarbons, MTBE and diethyl ether from the group consisting of the ethers, acetonitrile from the group consisting of the nitrites and ethyl acetate from the group consisting of the esters.

Mixtures of the solvents may also be present.

VC optionally contaminated with solvent is initially introduced as reaction medium, and CGC and tertiary amine, preferably triethylamine, are reacted therein at temperatures between 30 and 60° C., preferably between 40 and 50° C., one part of the crude mixture isolated by filtration preferably being used as reaction medium.

Usually, stirring is effected at the stated temperature for a period of 2 to 80, preferably 4 to 40, particularly preferably 5 to 15 hours.

The sequence of the metering of the components is in principle arbitrary; preferably, the amine is initially introduced in VC and the CGC metered in; particularly preferably, CGC and the amine are metered simultaneously.

In addition to the good yield, an advantage of the process is that the filter cake of the filtration of the precipitate of ammonium chloride produces no major filtration resistance.

The ammonium chloride salt isolated by filtration is freed from adhering reaction mixture by washing with an inert solvent. Crude reaction mixture and wash filtrate are fed to a vacuum distillation.

The free radical polymerization of VC can be suppressed by the addition of free radical scavengers, e.g. BHT.

Below, the process according to the invention is illustrated with reference to some examples, but the examples are to be understood as not limiting the concept of the invention.

EXAMPLES

Example 1

150 g of vinylene carbonate (about 99% pure), 31.2 g of triethylamine (99% pure) and 2 g of BHT were initially introduced into a thermostated 1 l pot having a plane-ground joint and were thermostated at 39° C., 283.5 g of triethylamine and 310 g of chloroethylene glycol carbonate (98% pure) were then metered in, in the course of 3 h and the internal temperature was kept below 45° C. by cooling. Thereafter, stirring was continued for 4 h at an internal temperature of 41 to 38° C.

Filtration was then effected over a suction filter at room temperature in vacuo.

283 g of an 82% strength crude VC filtrate was obtained.

The filter cake was then washed twice with 150 ml of MTBE each time.

The 1st wash filtrate contained 70 g of VC according to GC analysis.

The 2nd wash filtrate contained 4.3 g of VC according to GC analysis.

Together, this gave a yield of 73% of VC, minus initially introduced VC.

Example 2

275 g of vinylene carbonate (about 82% pure) and 2 g of BHT were initially introduced into a thermostated 1 l pot having a plane-ground joint and were thermostated at 37° C., 360 g of triethylamine (99% pure) and 400 g of chloroethylene glycol carbonate (98% pure) were then metered in in the course of 3 h and the internal temperature was kept below 45° C., followed by a subsequent stirring phase at 39° C. for 4 h.

After the salts had been filtered off at room temperature, 369 g of an 81% strength crude VC filtrate were obtained.

The filter cake was then washed twice with 150 ml of toluene each time.

The 1st wash filtrate contained 42 g of VC according to GC analysis.

The 2nd wash filtrate contained 5.2 g of VC according to GC analysis.

Together, this gave a yield of 74% of VC, minus initially introduced VC.

The filtration of the ammonium chloride precipitates was scarcely hindered by caking. The reactors had scarcely any deposits.

Example 3

Comparative Example 150 g of MTBE, 31.2 g of triethylamine (99% pure) and 2 g of BHT were initially introduced into a thermostated 1 l pot having a plane-ground joint and were thermostated at 39° C., 283.5 g of triethylamine and 310 g of chloroethylene glycol carbonate (98% pure) were then metered in in the course of 3 h and the internal temperature was kept below 45° C. by cooling. Thereafter, stirring was continued at an internal temperature of about 44° C. for 4 h.

Filtration was then effected over a suction filter at room temperature and the residue was rinsed with 100 ml of MTBE.

The combined liquids were distilled. Product-free first runnings of 485 g were obtained at 55-62° C.

92 g of a 95% strength crude vinylene carbonate was then obtained at 20 mbar and 66-84° C., which corresponded to a yield of 40.3% of theory.

Example 4

Comparative Example 150 g of MTBE, 31.2 g of triethylamine (99% pure) and 2 g of BHT were initially introduced into a thermostated 1 l pot having a plane-ground joint and were thermostated at 39° C., 283.5 g of triethylamine and 310 g of chloroethylene glycol carbonate (98% pure) were then metered in in the course of 3 h and the internal temperature was kept below 45° C. by cooling. Thereafter, stirring was continued at an internal temperature of about 42° C. for 20 h.

Filtration was then effected over a suction filter at room temperature and the residue was rinsed with 100 ml of MTBE.

The combined liquids weighed 490 g and were distilled. Product-free first runnings of 280 g were obtained at 55-62° C.

118 g of a 97.6% strength crude vinylene carbonate were obtained at 20 mbar and 59-65° C., which corresponded to a yield of 52.9% of theory.

92 g of a black tar remained behind.

Both comparative experiments showed pronounced caking on the vessel wall and stirrer.

| List of experiments on vinylene carbonate | |
| --- | --- |
| LRA | 6055 |
| LRA | 6058 |
| LRA | 6047 |
| LRA | 6048 |
| LRA | 6049 |
| LRA | 6046 |
| LRA | 7730 |
| LRA | 7733 |

The invention claimed is:

1. Process for the production of vinylene carbonate comprising eliminating hydrogen chloride from chloroethylene glycol carbonate (CGC) with tertiary amines, wherein the reaction is carried out at between 30 and 60° C. and wherein vinylene carbonate is used as the reaction medium, which optionally also contains up to 3% by weight of further solvent, based on the reaction medium.

2. The process according to claim 1, characterized in that the reaction is carried out at temperatures between 40 and 50° C.

3. The process according to claim 1, characterized in that the further solvent is MTBE, methylene chloride, toluene or acetonitrile.

4. Process for the production of vinylene carbonate comprising eliminating hydrogen chloride from chloroethylene glycol carbonate (CGC) with tertiary amines, wherein the reaction is carried out at between 30 and 60° C. and vinylene carbonate is used as the reaction medium and wherein the reaction takes place in the absence of additional solvents.

5. Process for the production of vinylene carbonate comprising eliminating hydrogen chloride from chloroethylene glycol carbonate (CGC) with tertiary amines, wherein the reaction is carried out at between 30 and 60° C. and wherein the reaction takes place in the absence of solvent.

* * * * *